(12) United States Patent
Nirogi et al.

(10) Patent No.: US 10,010,527 B2
(45) Date of Patent: Jul. 3, 2018

(54) ACTIVE METABOLITE OF 1-[(2-BROMOPHENYL)SULFONYL]-5-METHOXY-3-[(4-METHYL-1-PIPERAZINYL)METHYL]-1H-INDOLE DIMESYLATE MONOHYDRATE AND DIMESYLATE DIHYDRATE SALT OF ACTIVE METABOLITE

(71) Applicant: SUVEN LIFE SCIENCES LIMITED, Hyderabad, Andhra Pradesh (IN)

(72) Inventors: Ramakrishna Nirogi, Hyderabad (IN); Ramasastri Kambhampati, Hyderabad (IN); Anil Karbhari Shinde, Hyderabad (IN); Venkateswarlu Jasti, Hyderabad (IN)

(73) Assignee: SUVEN SCIENCES LIMITED, Hyderabad, Andhra (IN)

( * ) Notice: Subject to any disclaimer, the term of this patent is extended or adjusted under 35 U.S.C. 154(b) by 0 days.

(21) Appl. No.: 15/504,014

(22) PCT Filed: Oct. 20, 2014

(86) PCT No.: PCT/IN2014/000667
§ 371 (c)(1),
(2) Date: Feb. 14, 2017

(87) PCT Pub. No.: WO2016/027276
PCT Pub. Date: Feb. 25, 2016

(65) Prior Publication Data
US 2017/0273944 A1    Sep. 28, 2017

(30) Foreign Application Priority Data
Aug. 16, 2014 (IN) .......................... 4011/CHE/2014

(51) Int. Cl.
*A61K 31/4035* (2006.01)
*C07D 209/04* (2006.01)
*C07D 403/06* (2006.01)
*C07C 317/14* (2006.01)
*C07C 309/02* (2006.01)

(52) U.S. Cl.
CPC ........ *A61K 31/4035* (2013.01); *C07C 309/02* (2013.01); *C07C 317/14* (2013.01); *C07D 209/04* (2013.01); *C07D 403/06* (2013.01)

(58) Field of Classification Search
None
See application file for complete search history.

(56) References Cited

FOREIGN PATENT DOCUMENTS

| WO | 2004048330 A1 | 6/2004 |
|---|---|---|
| WO | 2004055026 A1 | 7/2004 |

OTHER PUBLICATIONS

European Patent Office, "International Search Report" and "Written Opinion", mailed in PCT Application No. PCT/IN2014/000667 dated Feb. 9, 2015.
European Patent Office, "International Preliminary Report on Patentability", mailed in PCT Application No. PCT/IN2014/000667 dated Feb. 26, 2016.

*Primary Examiner* — Heidi Reese
(74) *Attorney, Agent, or Firm* — IPHorgan Ltd.

(57) ABSTRACT

The present invention is directed to active metabolite of 1-[(2-bromophenyl)sulfonyl]-5-methoxy-3-[(4-methyl-1-piperazinyl)methyl]-1H-indole dimesylate monohydrate of formula (I). The present invention is also directed to dimesylate dihydrate salt of formula (II). The compounds of formula (I) and formula (II) are useful in the treatment of various disorders that are related to 5-HT$_6$ receptor antagonist.

15 Claims, 4 Drawing Sheets

☐ Vehicle, 2 mL/kg, *p.o.* + Vehicle 1 mL/kg, *i.p.*

▓ Vehicle, 2 mL/kg, *p.o.* + Scopolamine 0.8 mg/kg, *i.p.*

▤ Example 1, 5 mg/kg, *p.o.* + Scopolamine 0.8 mg/kg, *i.p.*

☰ Example 1, 10 mg/kg, *p.o.* + Scopolamine 0.8 mg/kg, *i.p.*

▨ Example 1, 20 mg/kg, *p.o.* + Scopolamine 0.8 mg/kg, *i.p.*

☐ Vehicle, 2 mL/kg, *p.o.* + Vehicle 1 mL/kg, *i.p.*
▦ Vehicle, 2 mL/kg, *p.o.* + Scopolamine 0.8 mg/kg, *i.p.*
▩ Example 2, 5 mg/kg, *p.o.* + Scopolamine 0.8 mg/kg, *i.p.*
☰ Example 2, 10 mg/kg, *p.o.* + Scopolamine 0.8 mg/kg, *i.p.*
▨ Example 2, 20 mg/kg, *p.o.* + Scopolamine 0.8 mg/kg, *i.p.*

ACTIVE METABOLITE OF 1-[(2-BROMOPHENYL)SULFONYL]-5-METHOXY-3-[(4-METHYL-1-PIPERAZINYL)METHYL]-1H-INDOLE DIMESYLATE MONOHYDRATE AND DIMESYLATE DIHYDRATE SALT OF ACTIVE METABOLITE

CROSS REFERENCE TO RELATED APPLICATIONS

This application is a national stage completion application of PCT Application No. PCT/IN2014/000667, filed Oct. 20, 2014, and claims the benefit of India Application No. 4011/CHE/2014, filed Aug. 16, 2014. Each of these applications is incorporated by reference herein in its entirety.

FIELD OF THE INVENTION

The present invention is directed to active metabolite of 1-[(2-bromophenyl)sulfonyl]-5-methoxy-3-[(4-methyl-1-piperazinyl)methyl]-1H-indole dimesylate monohydrate having the following structure

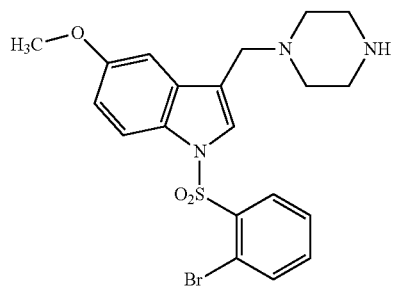

(I)

The present invention is also directed to dimesylate dihydrate salt of formula (I) having the following structure

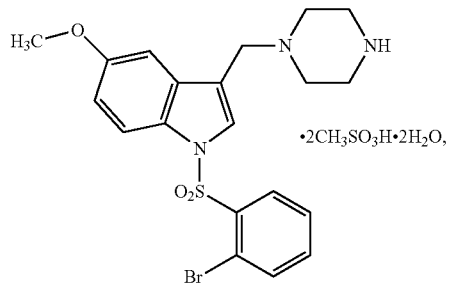

(II)

·2CH₃SO₃H·2H₂O,

The compounds of formula (I) and formula (II) are useful in the treatment of various disorders that are related to 5-HT$_6$ receptor antagonist.

BACKGROUND OF THE INVENTION

5-HT$_6$ receptor is one of the potential therapeutic target for the development of cognitive enhancers: for the treatment of Alzheimer's disease (AD) and schizophrenia. 5-HT$_6$ receptor is localized exclusively in central nervous system, in areas important for learning and memory. In recent years several studies (Brain Research, 1997, 746, 207-219; Journal of Neuroscience, 1998, 18(15), 5901-5907; International Review of Neurobiology Volume 96, 2011, 27-47 & Annual Reviews in Pharmacology and Toxicology, 2000, 40, 319-334a) have reported that 5-HT$_6$ receptor antagonists show beneficial effect on cognition in animal models.

Suven Life Sciences Ltd is developing 1-[(2-bromophenyl)sulfonyl]-5-methoxy-3-[(4-methyl-1-piperazinyl)methyl]-1H-indole dimesylate monohydrate, which is a selective 5-HT$_6$ receptor antagonists intended for the symptomatic treatment of AD and other disorders of memory and cognition like attention deficient hyperactivity, parkinson's and schizophrenia. 1-[(2-bromophenyl)sulfonyl]-5-methoxy-3-[(4-methyl-1-piperazinyl)methyl]-1H-indole, and its pharmaceutically acceptable salts were disclosed by Ramakrishna et al. in WO 2004/048330.

1-[(2-bromophenyl)sulfonyl]-5-methoxy-3-[(4-methyl-1-piperazinyl)methyl]-1H-indole dimesylate monohydrate has already completed Phase I clinical trials. Based on phase I clinical trials results, we confirmed 1-[(2-Bromophenyl)sulfonyl]-5-methoxy-3-[(1-piperazinyl)methyl]-1H-indole of formula (I) as an active metabolite of 1-[(2-bromophenyl)sulfonyl]-5-methoxy-3-[(4-methyl-1-piperazinyl)methyl]-1H-indole dimesylate monohydrate in human volunteers.

The development and understanding of the metabolism of 1-[(2-bromophenyl)sulfonyl]-5-methoxy-3-[(4-methyl-1-piperazinyl)methyl]-1H-indole dimesylate monohydrate is desirable for progression of science and necessary step in the commercialization of this compound. Therefore, there is a need to understand regarding metabolism and metabolites of 1-[(2-bromophenyl)sulfonyl]-5-methoxy-3-[(4-methyl-1-piperazinyl)methyl]-1H-indole dimesylate monohydrate.

In order to improve pharmaceutical properties and efficacy of active metabolite, we performed salt selection program for 1-[(2-Bromophenyl)sulfonyl]-5-methoxy-3-[(1-piperazinyl)methyl]-1H-indole. Based on the results obtained, dimesylate dihydrate salt of 1-[(2-Bromophenyl)sulfonyl]-5-methoxy-3-[(1-piperazinyl)methyl]-1H-indole of formula (II) is selected for further development along with the compound of formula (I).

SUMMARY OF THE INVENTION

The present invention is directed to active metabolite of 1-[(2-bromophenyl)sulfonyl]-5-methoxy-3-[(4-methyl-1-piperazinyl)methyl]-1H-indole dimesylate monohydrate having the following structure

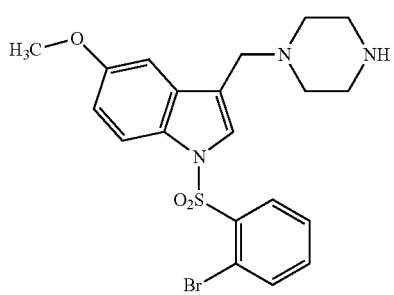

(I)

The present invention is also directed to dimesylate dihydrate salt of formula (I) having the following structure

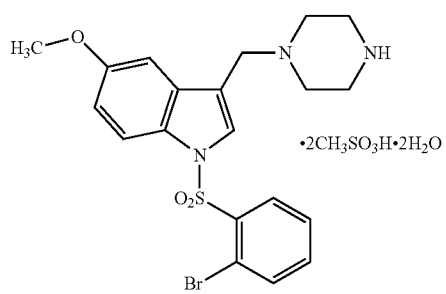

(II)

The present invention relates to use of a therapeutically effective amount of compounds of formula (I) and formula (II), to manufacture a medicament in the treatment of various disorders that are related to 5-HT$_6$ receptor antagonist.

Specifically, the compounds of formula (I) and formula (II) are useful in the treatment of various disorders such as AD, attention deficient hyperactivity, parkinson's and schizophrenia.

In another aspect, the invention relates to pharmaceutical compositions containing a therapeutically effective amount of compounds of formula (I) and formula (II) with pharmaceutically acceptable excipients.

In still another aspect, the invention relates to method of treatment of using compounds of formula (I) and formula (II).

In yet another aspect, the invention further relates to the process for preparing compounds of formula (I) and formula (II).

DETAILED DESCRIPTION OF THE INVENTION

Figure 1:
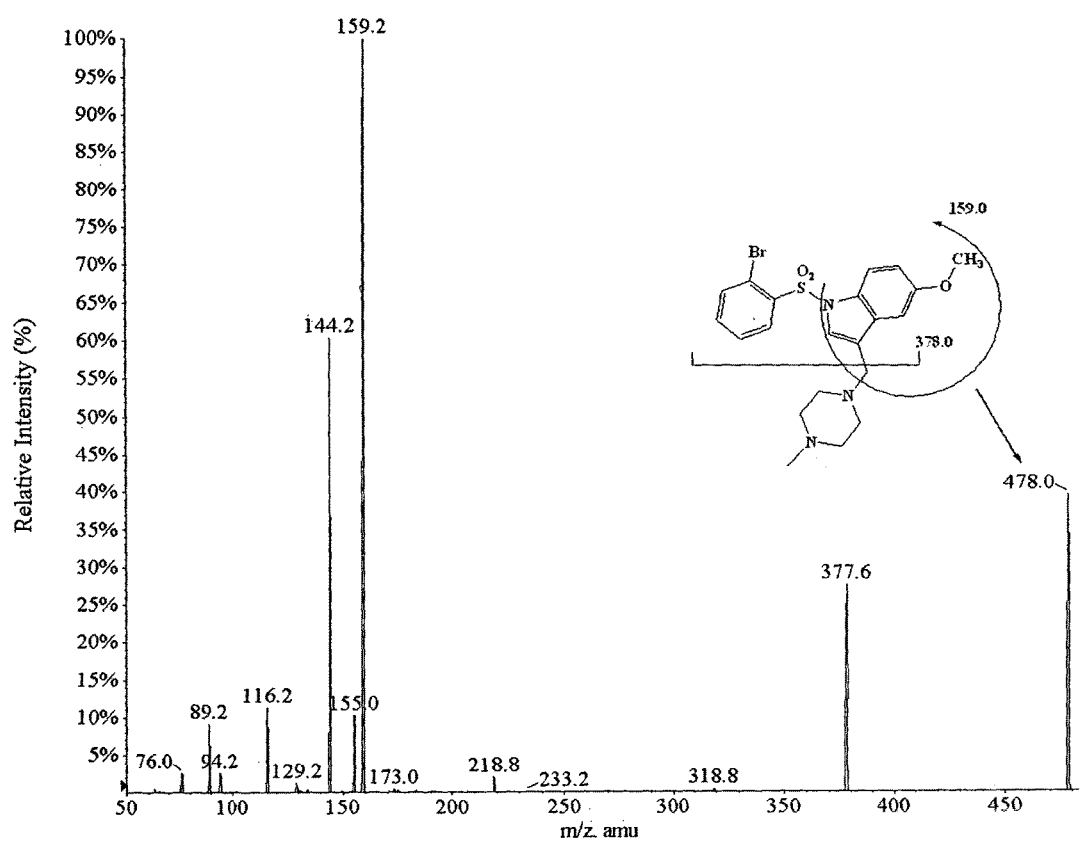
FIG. 1 illustrates the mass spectrum and MS-fragmented chemical structure of 1-[(2-bromophenyl)sulfonyl]-5-methoxy-3-[(4-methyl-1-piperazinyl)methyl]-1H-indole.
Figure 2:
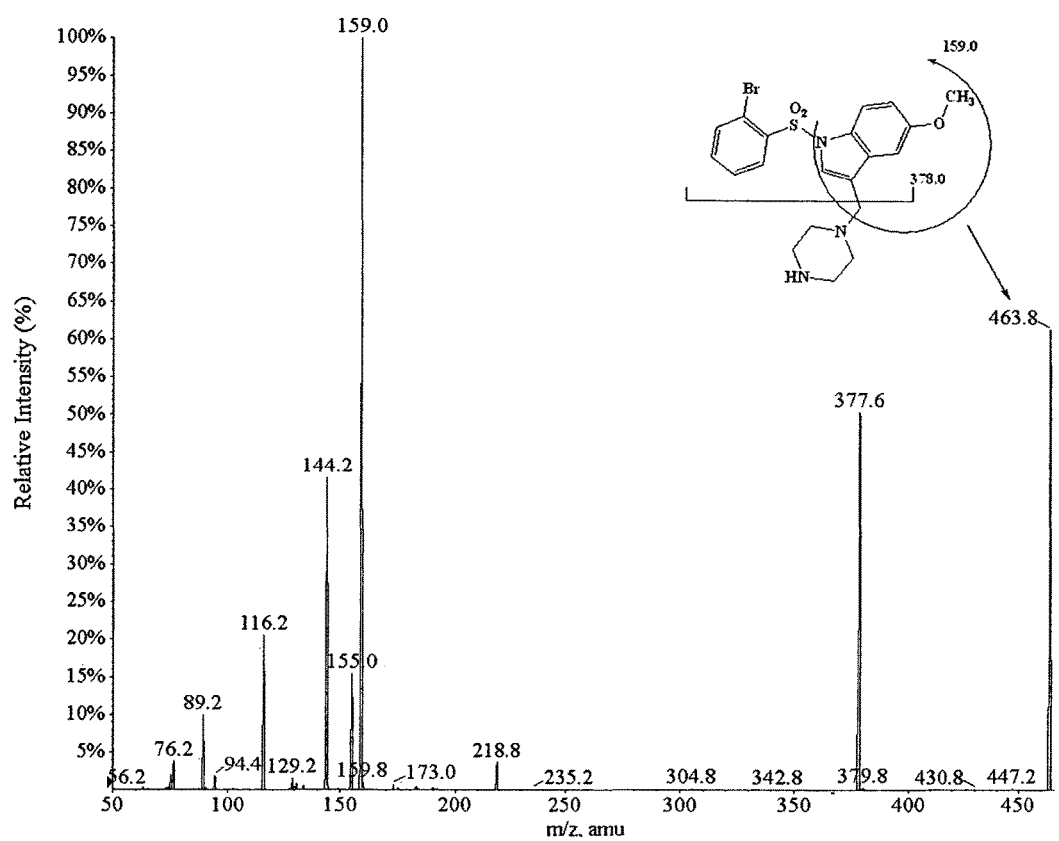
FIG. 2 illustrates the mass spectrum and MS-fragmented chemical structure of 1-[(2-Bromo phenyl)sulfonyl]-5-methoxy-3-[(1-piperazinyl)methyl]-1H-indole (Example 1).
Figure 3:
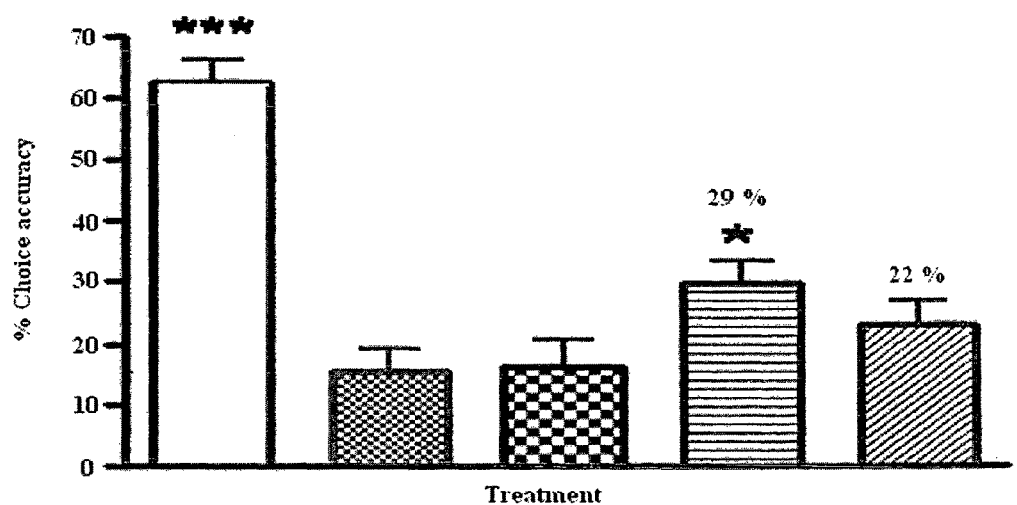
FIG. 3 illustrates the percentage choice accuracy of Example 1.
Figure 4:
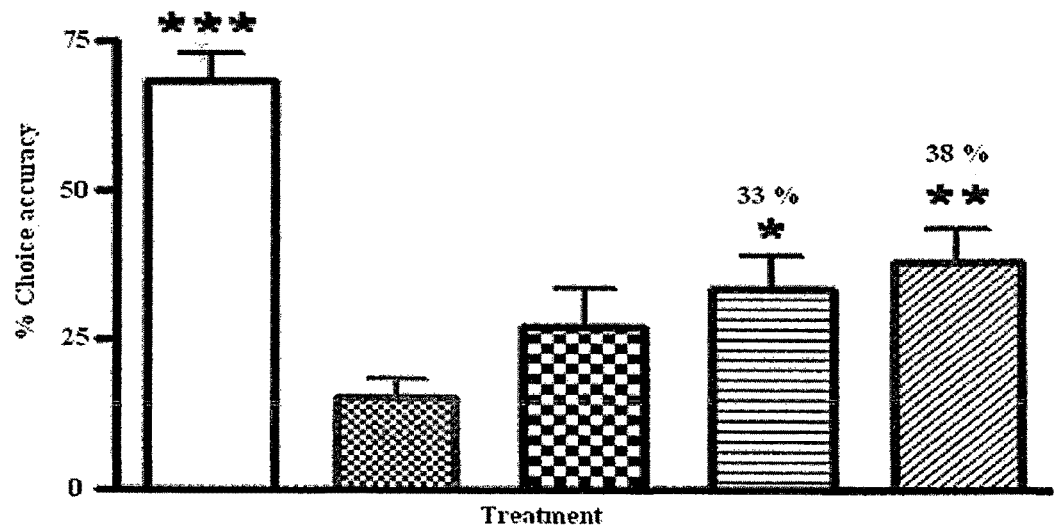
FIG. 4 illustrates the percentage choice accuracy of Example 2.

The term "antagonist" means full antagonist or partial antagonist.

The term "metabolite" refers to substance produced by metabolism.

The phrase "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

Commercial reagents were utilized without further purification. Room Temperature refers to 25-40° C. Unless otherwise stated, all mass spectra were obtained using ESI conditions. $^1$H-NMR spectra were recorded at 400 MHz on a Bruker instrument. Deuterated chloroform, methanol or dimethylsulfoxide was used as solvent. TMS was used as internal reference standard. Chemical shift values are expressed in parts per million (δ) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

Bioanalysis of Plasma Samples were Carried Using LC-MS/MS Method as Mentioned Below Solid Phase Extraction:

SPE cartridge Oasis HLB 1 cc, 30 mg (part. number #WAT058951) supplied by Waters, was used for the solid phase extraction.

Chromatographic Separation:

Analytical column: Zorbax Eclipse XDB C8, 4.6×150.0 mm, 5.0 μm.

Mobile phases: A: 10 mM Ammonium Acetate pH adjusted to 4.0±0.3 with formic acid B: Acetonitrile (100%, v/v).

The LC-MS was operated under the conditions listed in below Table:

| Parameters | Setting |
| --- | --- |
| Ionization | Pneumatically and thermally assisted ESI |
| Polarity | positive |
| Source | Sciex Turbo-V-Source |
| Spray voltage | 5500 V |
| Heater gas temperature | 350° C. (API 4000) |
| Gases | Nebulizer (air), heater (air), curtain (N2), collision (N2) |
| Scan mode | MRM |

Pharmaceutical Compositions

In order to use the compounds of formula (I) and formula (II) in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipient is carrier or diluent. Thus, the active compounds of the invention may be formulated for oral dosing. Such pharmaceutical compositions and processes for preparing the same are well known in the art (The Science and Practice of Pharmacy, D. B. Troy, 21$^{st}$ Edition, Williams & Wilkins, 2006).

The dose of the active compounds can vary depending on factors such as age and weight of patient, nature and severity of the disease to be treated and such other factors. Therefore, any reference regarding pharmacologically effective amount of the compounds of formula (I) and formula (II) refers to the aforementioned factors Methods of Preparation The compound of formula (I) can be prepared by using Scheme-I as shown below:

Scheme-I

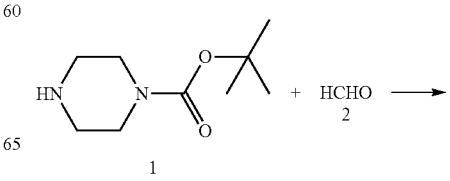

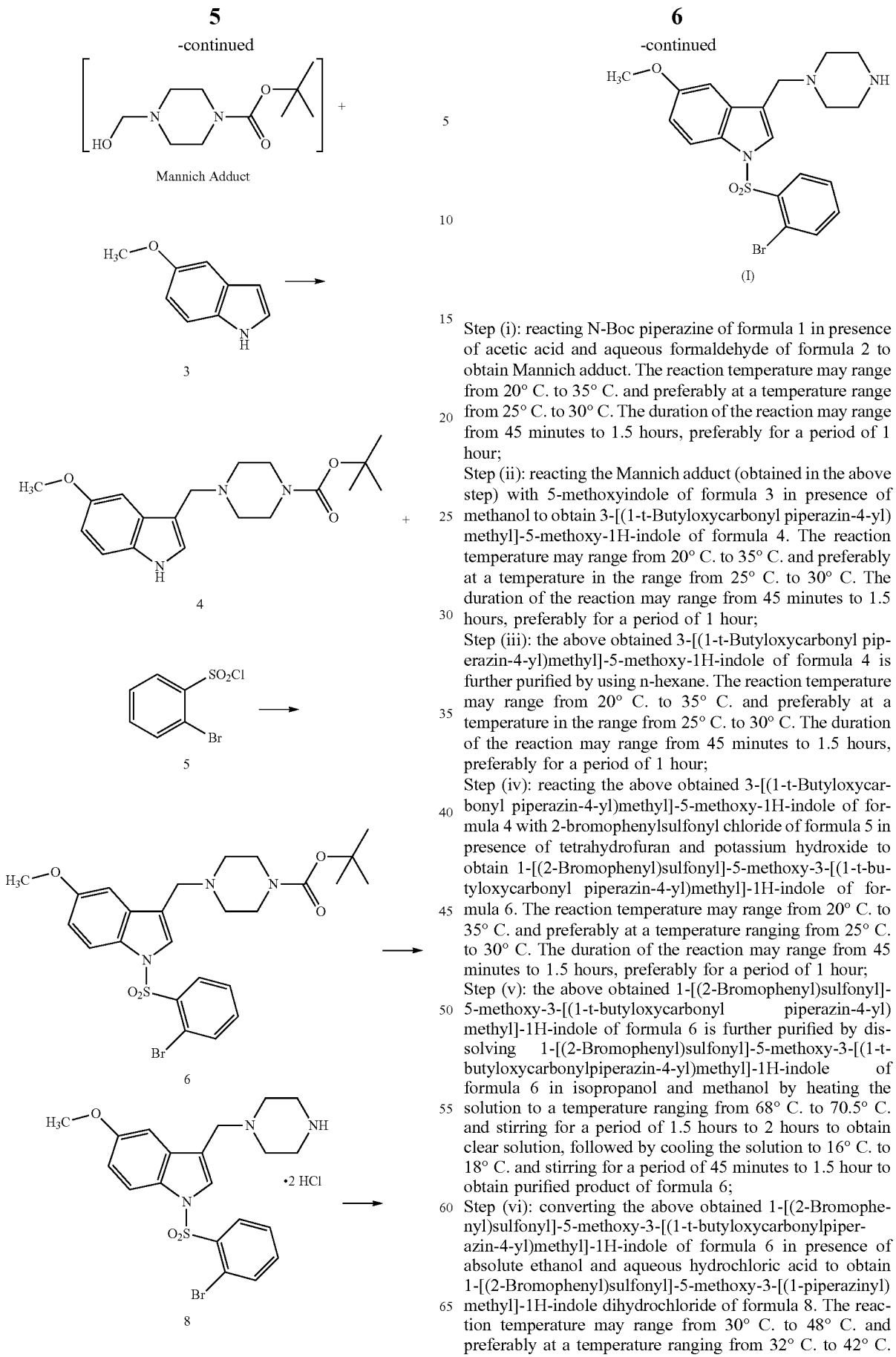

Step (i): reacting N-Boc piperazine of formula 1 in presence of acetic acid and aqueous formaldehyde of formula 2 to obtain Mannich adduct. The reaction temperature may range from 20° C. to 35° C. and preferably at a temperature range from 25° C. to 30° C. The duration of the reaction may range from 45 minutes to 1.5 hours, preferably for a period of 1 hour;

Step (ii): reacting the Mannich adduct (obtained in the above step) with 5-methoxyindole of formula 3 in presence of methanol to obtain 3-[(1-t-Butyloxycarbonyl piperazin-4-yl) methyl]-5-methoxy-1H-indole of formula 4. The reaction temperature may range from 20° C. to 35° C. and preferably at a temperature in the range from 25° C. to 30° C. The duration of the reaction may range from 45 minutes to 1.5 hours, preferably for a period of 1 hour;

Step (iii): the above obtained 3-[(1-t-Butyloxycarbonyl piperazin-4-yl)methyl]-5-methoxy-1H-indole of formula 4 is further purified by using n-hexane. The reaction temperature may range from 20° C. to 35° C. and preferably at a temperature in the range from 25° C. to 30° C. The duration of the reaction may range from 45 minutes to 1.5 hours, preferably for a period of 1 hour;

Step (iv): reacting the above obtained 3-[(1-t-Butyloxycarbonyl piperazin-4-yl)methyl]-5-methoxy-1H-indole of formula 4 with 2-bromophenylsulfonyl chloride of formula 5 in presence of tetrahydrofuran and potassium hydroxide to obtain 1-[(2-Bromophenyl)sulfonyl]-5-methoxy-3-[(1-t-butyloxycarbonyl piperazin-4-yl)methyl]-1H-indole of formula 6. The reaction temperature may range from 20° C. to 35° C. and preferably at a temperature ranging from 25° C. to 30° C. The duration of the reaction may range from 45 minutes to 1.5 hours, preferably for a period of 1 hour;

Step (v): the above obtained 1-[(2-Bromophenyl)sulfonyl]-5-methoxy-3-[(1-t-butyloxycarbonyl piperazin-4-yl) methyl]-1H-indole of formula 6 is further purified by dissolving 1-[(2-Bromophenyl)sulfonyl]-5-methoxy-3-[(1-t-butyloxycarbonylpiperazin-4-yl)methyl]-1H-indole of formula 6 in isopropanol and methanol by heating the solution to a temperature ranging from 68° C. to 70.5° C. and stirring for a period of 1.5 hours to 2 hours to obtain clear solution, followed by cooling the solution to 16° C. to 18° C. and stirring for a period of 45 minutes to 1.5 hour to obtain purified product of formula 6;

Step (vi): converting the above obtained 1-[(2-Bromophenyl)sulfonyl]-5-methoxy-3-[(1-t-butyloxycarbonylpiperazin-4-yl)methyl]-1H-indole of formula 6 in presence of absolute ethanol and aqueous hydrochloric acid to obtain 1-[(2-Bromophenyl)sulfonyl]-5-methoxy-3-[(1-piperazinyl) methyl]-1H-indole dihydrochloride of formula 8. The reaction temperature may range from 30° C. to 48° C. and preferably at a temperature ranging from 32° C. to 42° C.

The duration of the reaction may range from 6 to 10 hours, preferably for a period of 6 hours to 8 hours;

Step (vii): the above obtained 1-[(2-Bromophenyl)sulfonyl]-5-methoxy-3-[(1-piperazinyl)methyl]-1H-indole dihydrochloride of formula 8 is dissolved in water and basified to pH 10.5 to 11 by adding 40% (w/w) lye solution and extracted the product with ethyl acetate to obtain 1-[(2-Bromophenyl)sulfonyl]-5-methoxy-3-[(1-piperazinyl)methyl]-1H-indole of formula (I).

The compound of formula (II) can be prepared by using Scheme-II as shown below:

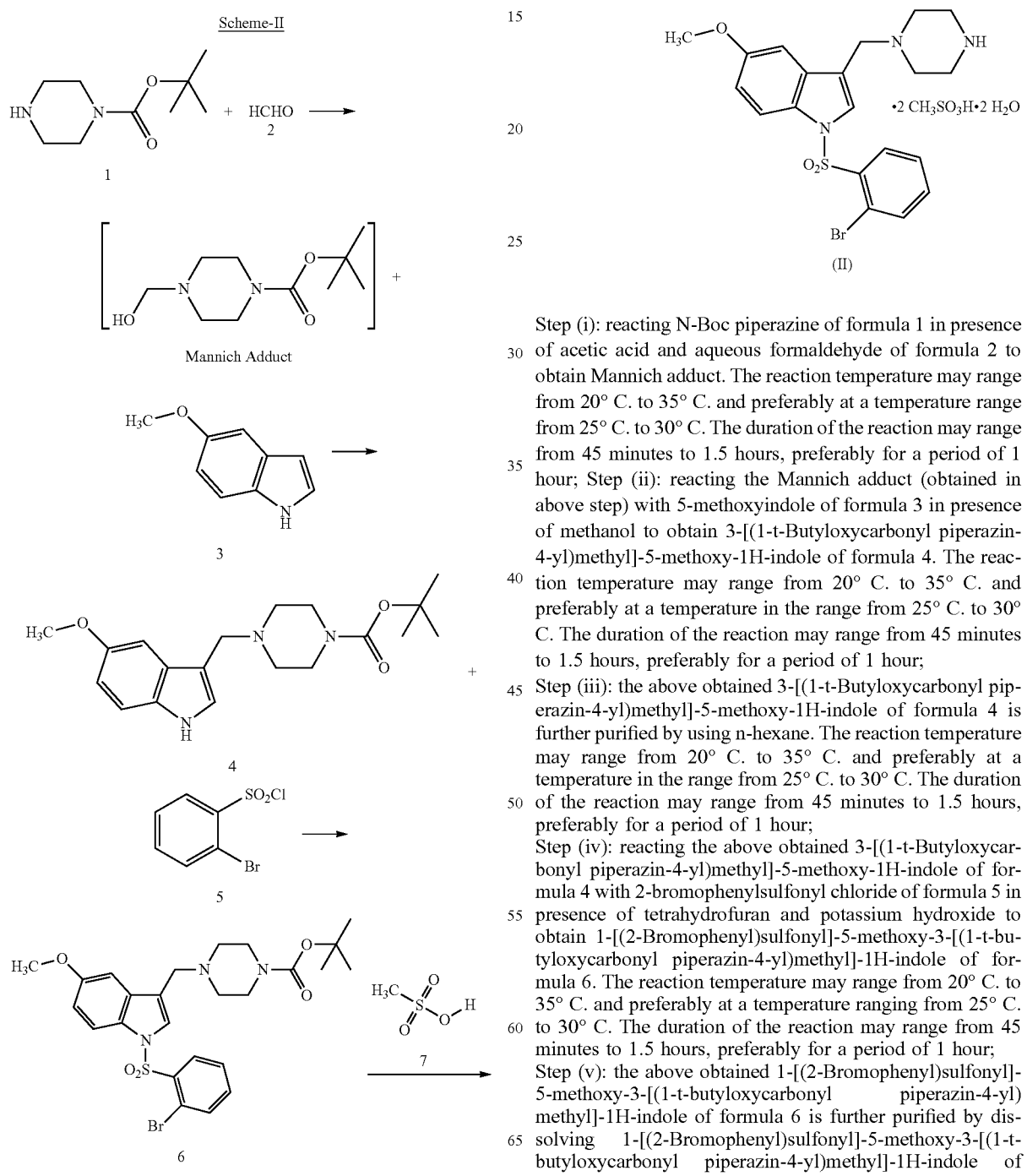

Step (i): reacting N-Boc piperazine of formula 1 in presence of acetic acid and aqueous formaldehyde of formula 2 to obtain Mannich adduct. The reaction temperature may range from 20° C. to 35° C. and preferably at a temperature range from 25° C. to 30° C. The duration of the reaction may range from 45 minutes to 1.5 hours, preferably for a period of 1 hour; Step (ii): reacting the Mannich adduct (obtained in above step) with 5-methoxyindole of formula 3 in presence of methanol to obtain 3-[(1-t-Butyloxycarbonyl piperazin-4-yl)methyl]-5-methoxy-1H-indole of formula 4. The reaction temperature may range from 20° C. to 35° C. and preferably at a temperature in the range from 25° C. to 30° C. The duration of the reaction may range from 45 minutes to 1.5 hours, preferably for a period of 1 hour;

Step (iii): the above obtained 3-[(1-t-Butyloxycarbonyl piperazin-4-yl)methyl]-5-methoxy-1H-indole of formula 4 is further purified by using n-hexane. The reaction temperature may range from 20° C. to 35° C. and preferably at a temperature in the range from 25° C. to 30° C. The duration of the reaction may range from 45 minutes to 1.5 hours, preferably for a period of 1 hour;

Step (iv): reacting the above obtained 3-[(1-t-Butyloxycarbonyl piperazin-4-yl)methyl]-5-methoxy-1H-indole of formula 4 with 2-bromophenylsulfonyl chloride of formula 5 in presence of tetrahydrofuran and potassium hydroxide to obtain 1-[(2-Bromophenyl)sulfonyl]-5-methoxy-3-[(1-t-butyloxycarbonyl piperazin-4-yl)methyl]-1H-indole of formula 6. The reaction temperature may range from 20° C. to 35° C. and preferably at a temperature ranging from 25° C. to 30° C. The duration of the reaction may range from 45 minutes to 1.5 hours, preferably for a period of 1 hour;

Step (v): the above obtained 1-[(2-Bromophenyl)sulfonyl]-5-methoxy-3-[(1-t-butyloxycarbonyl piperazin-4-yl)methyl]-1H-indole of formula 6 is further purified by dissolving 1-[(2-Bromophenyl)sulfonyl]-5-methoxy-3-[(1-t-butyloxycarbonyl piperazin-4-yl)methyl]-1H-indole of formula 6 in isopropanol and methanol by heating the solution to a temperature ranging from 68° C. to 70.5° C. and stirring for a period of 1.5 hours to 2 hours to obtain clear solution, followed by cooling the solution to 16° C. to 18° C. and stirring for a period of 45 minutes to 1.5 hour to obtain purified product of formula 6;

Step (vi): converting the above obtained 1-[(2-Bromophenyl)sulfonyl]-5-methoxy-3-[(1-t-butyloxycarbonyl piperazin-4-yl)methyl]-1H-indole of formula 6 in presence of acetone and methanesulfonic acid of formula 7 to obtain 1-[(2-Bromophenyl)sulfonyl]-5-methoxy-3-[(1-piperazinyl) methyl]-1H-indole dimesylate of formula 9. The reaction temperature may range from 20° C. to 35° C. and preferably at a temperature ranging from 25° C. to 30° C. The duration of the reaction may range from 3.5 to 4 hours, preferably for a period of 4 hours;

Step (vii): the above obtained 1-[(2-Bromophenyl)sulfonyl]-5-methoxy-3-[(1-piperazinyl) methyl]-1H-indole dimesylate of formula 9 is dissolved in water and acetone by heating the solution to 55° C. to 60° C., followed by cooling the solution to 30° C. to 35° C. and further cooling to 10° C. to 12° C. for the period of 1.5 hours to 2.5 hours to obtain 1-[(2-Bromophenyl)sulfonyl]-5-methoxy-3-[(1-piperazinyl) methyl]-1H-indole dimesylate dihydrate of formula (II).

Example 1: Preparation of 1-[(2-Bromophenyl)sulfonyl]-5-methoxy-3-[(1-piperazinyl)methyl]-1H-indole

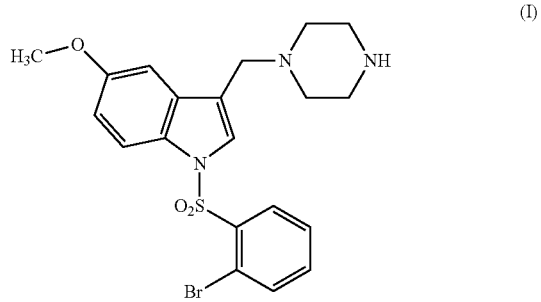 [SMILES: COc1ccc2c(c1)c(CN1CCNCC1)cn2S(=O)(=O)c1ccccc1Br]

Step (i) & (ii): Preparation of 3-[(1-t-Butyloxycarbonyl piperazin-4-yl)methyl]-5-methoxy-1H-indole

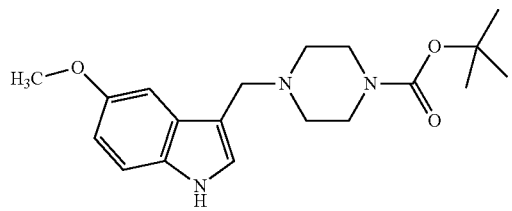 [SMILES: COc1ccc2[nH]cc(CN3CCN(C(=O)OC(C)(C)C)CC3)c2c1]

Step (i):

Demineralized water (DM water) (660 mL) and N-Boc piperazine (150.0 grams, 0.8034 moles) were charged into a 2 Liters three necked round bottomed flask provided with a mechanical stirrer and a thermometer pocket. The mass was stirred for 10 minutes at 25° C., to obtain a clear solution. Then acetic acid (32.5 mL, 0.5416 moles) was added to the above mass while maintaining the mass temperature at ~25° C. in 10 minutes. After completion of addition, the clear solution was stirred at 25° C. for 30 minutes.

To the above stirred mass at 25° C., aqueous formaldehyde solution (81 mL, 30% w/v, 0.81 moles) was added slowly through an addition funnel over a period of 30 minutes maintaining the mass temperature below 25° C. During the addition, white slurry mass was formed. The resultant white slurry mass was stirred for another 1 hour at 25-30° C. Methanol (MeOH) (300 mL) was added to the above mass to obtain a clear solution. The solution was further stirred for 30 minutes at 25° C. to obtain Mannich adduct.

Step (ii):

5-Methoxyindole (106.4 grams, 0.7238 moles) and methanol (550 mL) were charged into a 4 necked round bottom flask. The mass was stirred for 10 minutes at 25° C. to obtain a clear solution and then cooled the mass to 18-20° C. The mannich adduct (prepared in above step) was added to the flask through an addition funnel maintaining mass temperature below 20° C., over a period of 1 hour. The mass was further stirred for a period of 1 hour at 25-30° C., while monitoring the progress of the reaction by thin layer chromatography (TLC).

After completion of the reaction (1 hour), DM water (2.2 Liters) and ethyl acetate (1 Liter) were added to the reaction mass and pH adjusted to 10.5 (on pH paper) with lye solution (80 mL) maintaining the mass temperature at 20-24° C. The organic (product) layer was separated and the aqueous layer was further extracted with ethyl acetate (2×500 mL). The combined organic layer was washed with saturated brine solution (300 mL) and dried over anhydrous sodium sulfate. The organic layer was filtered free of sodium sulfate and concentrated under reduced pressure. n-Hexane (300 mL) was added to the residual mass and further concentrated under vacuum for removal of traces of ethyl acetate to obtain 272.2 grams of technical product.

Purity: 96.16%;

$^1$H-NMR (CDCl$_3$, δ ppm): 1.45 (9H, s), 2.44 (4H, bm), 3.41-3.43 (4H, bm), 3.69 (2H, s), 3.87 (3H, s), 6.85-6.88 (1H, dd, J=8.75, 2.23 Hz), 7.10 (1H, d, J=0.96 Hz), 7.19 (1H, d, J=2.24 Hz), 7.24-7.26 (1H, d), 8.04 (1H, bs);

Mass [M+H]$^+$: 346.2.

Step (iii): Purification of 3-[(1-t-Butyloxycarbonyl piperazin-4-yl)methyl]-5-methoxy-1H-indole n-Hexane (1.25 Liters) was taken in 2 Liters four necked round bottom flask equipped with thermometer pocket and mechanical stirrer and charged the above obtained technical compound (270.9 grams). The mass was stirred for 1 hour at 25° C. The product was filtered through Buckner funnel under vacuum. The compound was washed with n-hexane (2×125 mL), sucked well and air dried at 25° C. for 20 hours to obtain 240.0 grams of above title compound. Yield: 96%;

Purity: 97.09%;

$^1$H-NMR (CDCl$_3$, δ ppm): 1.45 (9H, s), 2.45 (4H, s), 3.43 (4H, s), 3.69 (2H, s), 3.86 (3H, s), 6.85-6.88 (1H, dd, J=8.7, 2.2 Hz), 7.08-7.09 (1H, d, J=1.57 Hz), 7.19 (1H, d, J=2.2 Hz), 7.23-7.25 (1H, d, J=8.77 Hz), 8.25 (1H, bs);

Mass [M+H]$^+$: 346.2.

Step (iv): Preparation of 1-[(2-Bromophenyl)sulfonyl]-5-methoxy-3-[(1-t-butyloxycarbonyl piperazin-4-yl)methyl]-1H-indole

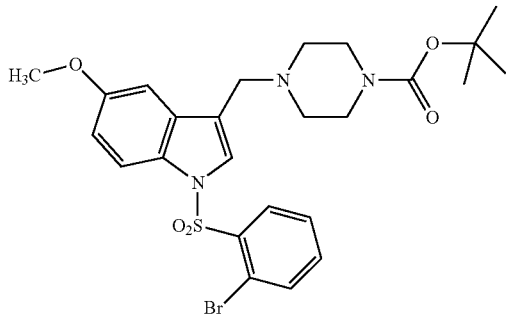 [SMILES: COc1ccc2c(c1)c(CN1CCN(C(=O)OC(C)(C)C)CC1)cn2S(=O)(=O)c1ccccc1Br]

Tetrahydrofuran (THF) (4.6 Liters) was charged into a reactor at 25° C., followed by the addition of powdered potassium hydroxide (860.6 grams, 85%, 13.06 moles) at 25° C. under stirring. TNT (3 Liters) was charged into a 5 Liters, three necked round bottom flask, provided with a mechanical stirrer and thermometer pocket. 3-[(1-t-Butyloxycarbonyl piperazin-4-yl) methyl]-5-methoxy-1H-indole (obtained in above step) (1287.7 grams, 3.7324 moles) was charged into the flask at 25° C. and stirred the mass well for complete dissolution. Then the clear 3-[(1-t-Butyloxycarbonyl piperazin-4-yl) methyl]-5-methoxy-1H-indole solution, prepared as above, was slowly transferred to the reactor containing potassium hydroxide under stirring, maintaining the mass temperature below 25° C. After completion of the addition, the reaction mass was stirred at 25° C. for 2 hours. A solution of 2-bromophenylsulfonyl chloride (1293.04 grams, 5.062 moles) dissolved in THF (2.0 Liters) was added to the reaction mass through an addition funnel at a constant rate in 30 minutes, maintaining the mass temperature at 20-32° C. The reaction was exothermic in nature. The mass was further stirred for 1 hour at 25-30° C.

As the reaction was progressing the mass thickened due to formation of potassium chloride. The progress of the reaction was monitored by TLC (Eluent system: Ethyl acetate) and the product is relatively non-polar. The starting material was absent as per TLC. A second lot of 2-bromophenylsulfonyl chloride (52.5 grams, dissolved in 100 mL of THF) was added to the reaction mass at 28° C. and further stirred the mass at 28° C. for another hour to ensure completion of the reaction. The reaction mass was unloaded into neat carboys.

Ice-water (40 Liters) was charged into a clean reactor and the reaction mass unloaded in the carboys was quenched into the reactor under stirring and the pH of the resulting solution was found to be 11.5 (pH paper). The product was extracted with (15 Liters+7.5 Liters+7.5 Liters) ethyl acetate. The combined organic layer was washed with saturated brine solution (2×5 L) and dried over anhydrous sodium sulfate. Total volume of the organic layer was 30 Liters. A small portion of the organic layer was concentrated in laboratory and the solid obtained was analyzed to check the quality of the technical product.

Purity: 91.46%;
$^1$H-NMR (CDCl$_3$, δ ppm): 1.45 (9H, s), 2.42-2.43 (4H, bs), 3.42 (4H, bs), 3.62 (2H, s), 3.81 (3H, s), 6.83-6.86 (1H, m), 7.18-7.19 (1H, m), 7.38-7.45 (2H, m), 7.52-7.55 (1H, m), 7.64-7.66 (2H, m), 8.06-8.08 (1H, d, J=7.76 Hz);
Mass [M+H]$^+$: 564.3, 566.4.

The organic layer, was taken for further workup and the technical product was purified without isolation.

Step (v): Purification of 1-[(2-Bromophenyl)sulfonyl]-5-methoxy-3-[(1-t-butyloxycarbonyl piperazin-4-yl)methyl]-1H-indole The above organic layer was filtered (30 Liters) and charged into a reactor. Solvent was distilled off under vacuum at 40-45° C. to obtain solids. Isopropanol (14 Liters) and methanol (7 Liters) were charged into the reactor containing the solid product. The reaction mass was heated to reflux temperature (70.5° C.) under stirring and further stirred the mass at reflux for two hours to ensure formation of clear solution.

Reaction mass was then slowly cooled to room temperature (30 minutes) with room temperature water circulation in the jacket. It was further cooled to 18° C. and stirred for 1 hour. The product was centrifuged and the cake on the centrifuge was washed with isopropanol/methanol mixture (1.6 Liters+0.8 Liters). It was sucked well and air dried at 40-45° C. for 4 hours in tray driers.

Weight of compound: 1554.8 grams, Cream colored crystalline powder, Yield: 77.7%
Purity: 99.42%;
$^1$H-NMR (CDCl$_3$, δ ppm): 1.45 (9H, s), 2.42 (4H, bs), 3.42 (4H, bs), 3.63 (2H, s), 3.82 (3H, s), 6.83-6.86 (1H, dd, J=8.34, 2.09 Hz), 7.19 (1H, d, J=2.0 Hz), 7.36-7.40 (1H, t, J=7.14 Hz), 7.43-7.47 (1H, t, J=7.56 Hz), 7.52-7.55 (1H, d, J=8.95 Hz), 7.64-7.66 (2H, m), 8.06-8.08 (1H, d, J=7.87 Hz); Mass: [M+H]$^+$: 564.3, 566.3.

Step (vi): Preparation of 1-[(2-bromophenyl)sulfonyl]-5-methoxy-3-[(1-piperazinyl)methyl]-1H-indole dihydrochloride

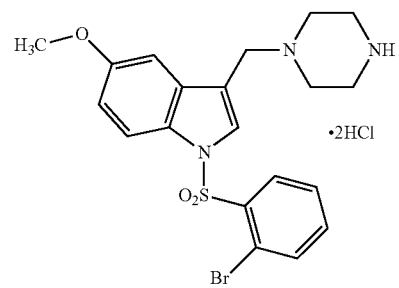

8

1-[(2-Bromophenyl)sulfonyl]-5-methoxy-3-[(4-t-butyloxycarbonyl-1-piperazinyl)methyl]-1H-indole (20.2 grams, 0.03578 M, obtained in the above step) was suspended in 250 mL of absolute ethanol at 25° C. and then added 20 mL of 30% (w/w) aqueous, hydrochloric acid drop wise under stirring over a period of 30 minutes, whereby a clear solution was obtained. The reaction was exothermic and temperature went up to 38° C. The mass was further heated at reflux for 4 hours. During this period solids separated. The mass was stirred for another 2 hours at reflux. The progress of the reaction was monitored by thin layer chromatography. After completion of the reaction, the mass was cooled to 25° C. and filtered the solids under suction. The solid on the filter was washed with 30 mL of absolute ethanol and the mass was dried under rotavacuum at 40-45° C. for 1 hour to obtain 1-[(2-bromophenyl)sulfonyl]-5-methoxy-3-[(1-piperazinyl) methyl]-1H-indole dihydrochloride (19.28 grams).
Purity: 99.8%,
Mass: [M+H]+: 464.2, 466.2.

Step (vii): Preparation of 1-[(2-bromophenyl)sulfonyl]-5-methoxy-3-[(1-piperazinyl)methyl]-1H-indole The above obtained compound (19.09 grams) was suspended in demineralised water (300 mL) and cooled to 15-20° C. The mass was basified to pH 10.5 to 11.0 by adding 40% (w/w) lye solution, maintaining mass temperature below 20° C. under nitrogen atmosphere. The product was extracted with (2×150 mL) ethylacetate. The combined organic layer was washed with (100 mL) saturated brine solution, dried over anhydrous sodium sulfate and solvent removed under rotavacuum at 40-45° C. to obtain the title compound (15.91 grams).
Yield: 96.4%
Purity: 99.89%,
DSC (5° C./minutes): 99.6° C.;
TGA (5° C./minutes): 0.76%;
1H-NMR (CDCl3, δ ppm): 1.85 (1H, s), 2.44 (4H, bs), 2.86-2.88 (4H, t), 3.59 (2H, s), 3.76 (3H, s), 6.82-6.84 (1H, J=9.0, 2.45 Hz), 7.20-7.21 (1H, d, J=2.28 Hz), 7.33-7.37 (1H, dt, J=7.48 Hz), 7.41-7.44 (1H, t), 7.52-7.54 (1H, d, J=7.65 Hz), 7.62-7.64 (2H, m), 8.01-8.03 (1H, dd, J=7.98, 1.15 Hz);
Mass: [M+H]+: 464.2, 466.2.

Example 2: Preparation of 1-[(2-Bromophenyl)sulfonyl]-5-methoxy-3-[(1-piperazinyl)methyl]-1H-indole dimesylate dihydrate

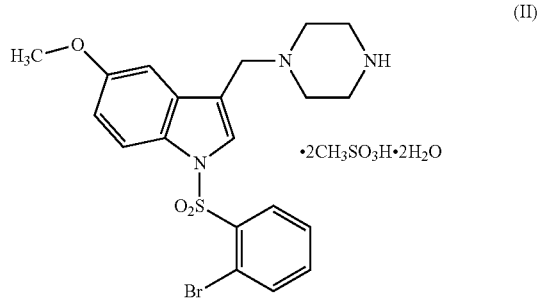 [SMILES: COc1ccc2c(c1)c(CN1CCNCC1)cn2S(=O)(=O)c1ccccc1Br]

(II)

·2CH3SO3H·2H2O

Step (i) & (ii): Preparation of 3-[(1-t-Butyloxycarbonyl piperazin-4-yl)methyl]-5-methoxy-1H-indole

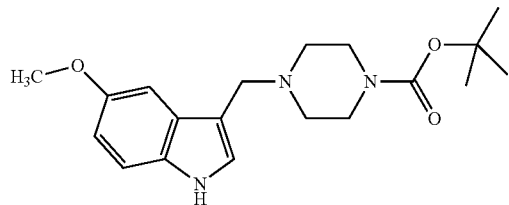 [SMILES: COc1ccc2[nH]cc(CN3CCN(C(=O)OC(C)(C)C)CC3)c2c1]

Step (i):
Demineralized water (DM water) (660 mL) and N-Boc piperazine (150.0 grams, 0.8034 moles) were charged into a 2 Liters three necked round bottomed flask provided with a mechanical stirrer and a thermometer pocket. The mass was stirred for 10 minutes at 25° C., to obtain a clear solution. Then acetic acid (32.5 mL, 0.5416 moles) was added to the above mass while maintaining the mass temperature at 25° C. in 10 minutes. After completion of addition, the clear solution was stirred at 25° C. for 30 minutes.
To the above stirred mass at 25° C., aqueous formaldehyde solution (81 mL, 30 w/v, 0.81 moles) was added slowly through an addition funnel over a period of 30 minutes maintaining the mass temperature below 25° C. During the addition, white slurry mass was formed. The resultant white slurry mass was stirred for another 1 hour at 25-30° C. Methanol (MeOH) (300 mL) was added to the above mass to obtain a clear solution. The solution was further stirred for 30 minutes at 25° C. to obtain Mannich adduct.
Step (ii):
5-Methoxy indole (106.4 grams, 0.7238 moles) and methanol (550 mL) were charged into a 4 necked round bottom flask. The mass was stirred for 10 minutes at 25° C. to obtain a clear solution and then cooled the mass to 18-20° C. The mannich adduct (prepared in above step) was added to the flask through an addition funnel maintaining mass temperature below 20° C., over a period of 1 hour. The mass was further stirred for a period of 1 hour at 25-30° C., while monitoring the progress of the reaction by thin layer chromatography (TLC).
After completion of the reaction (1 hour), DM water (2.2 Liters) and ethyl acetate (1 Liter) were added to the reaction mass and pH adjusted to 10.5 (on pH paper) with lye solution (80 mL) maintaining the mass temperature at 20-24° C. The organic (product) layer was separated and the aqueous layer was further extracted with ethyl acetate (2×500 mL). The combined organic layer was washed with saturated brine solution (300 mL) and dried over anhydrous sodium sulfate. The organic layer was filtered free of sodium sulfate and concentrated under reduced pressure. n-Hexane (300 mL) was added to the residual mass and further concentrated under vacuum for removal of traces of ethyl acetate to obtain 272.2 grams of technical product.
Purity: 96.16%;
1H-NMR (CDCl3, δ ppm): 1.45 (9H, s), 2.44 (4H, bm), 3.41-3.43 (4H, bm), 3.69 (2H, s), 3.87 (3H, s), 6.85-6.88 (1H, dd, J=8.75, 2.23 Hz), 7.10 (1H, d, J=0.96 Hz), 7.19 (1H, d, J=2.24 Hz), 7.24-7.26 (1H, d), 8.04 (1H, bs);
Mass [M+H]+: 346.2.

Step (iii): Purification of 3-[(1-t-Butyloxycarbonyl piperazin-4-yl)methyl]-5-methoxy-1H-indole n-Hexane (1.25 Liters) was taken in 2 Liters four necked round bottom flask equipped with thermometer pocket and mechanical stirrer and charged the above obtained technical compound (270.9 grams). The mass was stirred for 1 hour at 25° C. The product was filtered through Buckner funnel under vacuum. The compound was washed with n-hexane (2×125 mL), sucked well and air dried at 25° C. for 20 hours to obtain 240.0 grams of above title compound. Yield: 96%;
Purity: 97.09%;
1H-NMR (CDCl3, δ ppm): 1.45 (9H, s), 2.45 (4H, s), 3.43 (4H, s), 3.69 (2H, s), 3.86 (3H, s), 6.85-6.88 (1H, dd, J=8.7, 2.2 Hz), 7.08-7.09 (1H, d, J=1.57 Hz), 7.19 (1H, d, J=2.2 Hz), 7.23-7.25 (1H, d, J=8.77 Hz), 8.25 (1H, bs);
Mass [M+H]+: 346.2.

Step (iv): Preparation of 1-[(2-Bromophenyl)sulfonyl]-5-methoxy-3-[(1-t-butyloxycarbonyl piperazin-4-yl)methyl]-1H-indole

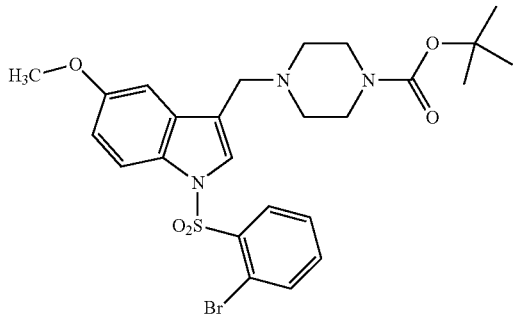 [SMILES: COc1ccc2c(c1)c(CN1CCN(C(=O)OC(C)(C)C)CC1)cn2S(=O)(=O)c1ccccc1Br]

Tetrahydrofuran (THF) (4.6 Liters) was charged into a reactor at 25° C., followed by the addition of powdered potassium hydroxide (860.6 grams, 85%, 13.06 moles) at 25° C. under stirring. THF (3 Liters) was charged into a 5 Liters, three necked round bottom flask, provided with a mechanical stirrer and thermometer pocket. 3-[(1-t-Butyloxycarbonyl piperazin-4-yl)methyl]-5-methoxy-1H-indole (obtained in above step) (1287.7 grams, 3.7324 moles) was charged into the flask at 25° C. and stirred the mass well for complete dissolution. Then the clear 3-[(1-t-Butyloxycarbonyl piperazin-4-yl)methyl]-5-methoxy-1H-indole solution, prepared as above, was slowly transferred to the reactor containing potassium hydroxide under stirring, maintaining the mass temperature below 25° C. After completion of the addition, the reaction mass was stirred at 25° C. for 2 hours. A solution of 2-bromophenylsulfonyl chloride (1293.04 grams, 5.062 moles) dissolved in THF (2.0 Liters) was added to the reaction mass through an addition funnel at a constant rate in 30 minutes, maintaining the mass temperature at 20-32° C. The reaction was exothermic in nature. The mass was further stirred for 1 hour at 25-30° C.

As the reaction was progressing the mass thickened due to formation of potassium chloride. The progress of the reaction was monitored by TLC (Eluent system: Ethyl acetate) and the product is relatively non-polar. The starting material was absent as per TLC. A second lot of 2-bromophenylsulfonyl chloride (52.5 grams, dissolved in 100 mL of THF) was added to the reaction mass at 28° C. and further stirred the mass at 28° C. for another hour to ensure completion of the reaction. The reaction mass was unloaded into neat carboys.

Ice-water (40 Liters) was charged into a clean reactor and the reaction mass unloaded in the carboys was quenched into the reactor under stirring and the pH of the resulting solution was 11.5 (pH paper). The product was extracted with (15 Liters+7.5 Liters+7.5 Liters) ethyl acetate. The combined organic layer was washed with saturated brine solution (2×5 L) and dried over anhydrous sodium sulfate. Total volume of the organic layer was 30 Liters. A small portion of the organic layer was concentrated in laboratory and the solid obtained was analyzed to check the quality of the technical product.

Purity: 91.46%;
$^1$H-NMR (CDCl$_3$, δ ppm): 1.45 (9H, s), 2.42-2.43 (4H, bs), 3.42 (4H, bs), 3.62 (2H, s), 3.81 (3H, s), 6.83-6.86 (1H, m), 7.18-7.19 (1H, m), 7.38-7.45 (2H, m), 7.52-7.55 (1H, m), 7.64-7.66 (al, m), 8.06-8.08 (1H, d, J=7.76 Hz);
Mass [M+H]$^+$: 564.3, 566.4.

The organic layer was taken for further workup and the technical product was purified without isolation.

Step (v): Purification of 1-[(2-Bromophenyl)sulfonyl]-5-methoxy-3-[(1-t-butyloxycarbonyl piperazin-4-yl)methyl]-1H-indole The above organic layer was filtered (30 Liters) and charged into a reactor. Solvent was distilled off under vacuum at 40-45° C. to obtain solids. Isopropanol (14 Liters) and methanol (7 Liters) were charged into the reactor containing the solid product. The reaction mass was heated to reflux temperature (70.5° C.) under stirring and further stirred the mass at reflux for two hours to ensure formation of clear solution.

Reaction mass was then slowly cooled to room temperature (30 minutes) with room temperature water circulation in the jacket. It was further cooled to 18° C. and stirred for 1 hour. The product was centrifuged and the cake on the centrifuge was washed with isopropanol/methanol mixture (1.6 Liters+0.8 Liters). It was sucked well and air dried at 40-45° C. for 4 hours in tray driers.

Weight of compound: 1554.8 grams, Cream colored crystalline powder, Yield: 77.7%
Purity: 99.42%;
$^1$H-NMR (CDCl$_3$, δ ppm): 1.45 (9H, s), 2.42 (4H, bs), 3.42 (4H, bs), 3.63 (2H, s), 3.82 (3H, s), 6.83-6.86 (1H, dd, J=8.34, 2.09 Hz), 7.19 (1H, d, J=2.0 Hz), 7.36-7.40 (1H, t, J=7.14 Hz), 7.43-7.47 (1H, t, J=7.56 Hz), 7.52-7.55 (1H, d, J=8.95 Hz), 7.64-7.66 (2H, m), 8.06-8.08 (1H, d, J=7.87 Hz); Mass: [M+H]$^+$: 564.3, 566.3.

Step (vi): Preparation of 1-[(2-Bromophenyl)sulfonyl]-5-methoxy-3-[(1-piperazinyl)methyl]-1H-indole dimesylate

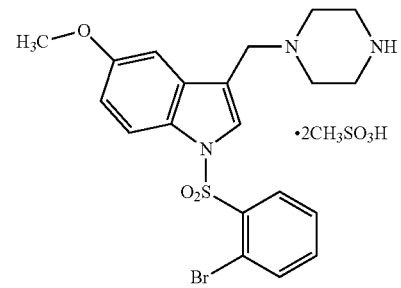

1-[(2-Bromophenyl)sulfonyl]-5-methoxy-3-[(1-t-butyloxycarbonyl piperazin-4-yl)methyl]-1H-indole (obtained in the above step, 1540 grams, 2.73 mole) was dissolved in acetone (30.8 Liters) and charged into a glass lined reactor. The temperature of the reaction mass was raised to reflux temperature (56° C.). Methanesulfonic acid (920 grams, 9.57 moles) diluted with acetone (6 Liters) was added to the above mass at reflux temperature, slowly over a period of 30 minutes, through an addition funnel. During addition vigorous reflux was observed. The reaction mass was a clear solution before and after the addition of methanesulfonic acid solution. After stirring for ~90 minutes at reflux, thick mass of solids separated out. The progress of the reaction was monitored by TLC. The reaction was completed in 4 hours. Then the mass was cooled to 25° C. and further stirred for two hours at 25° C. The product was filtered through nutsche filter under vacuum. The product on the nutsche filter was washed with acetone (8 Liters). The material was unloaded into trays and air dried at 30-35° C. for 4 hours in a tray drier. Weight of the product: 1.61 Kg (off white with pinkish tinge).

Yield: 90%;
Salt content (dimesylate): 32.1% w/w;
Purity: 99.97%;
$^1$H-NMR (D$_2$O, δ ppm): 2.64 (6H, s), 3.48 (4H, bs), 3.53 (4H, bs), 3.70 (3H, s), 4.50 (2H, s), 6.75-6.78 (1H, dd, =8.97, 1.92 Hz), 7.11 (1H, d, J=1.78 Hz), 7.32-7.34 (1H, t, J=9.28 Hz), 7.34-7.38 (1H, t, J=7.63 Hz), 7.44-7.48 (1H, d, J=7.76 Hz), 7.54-7.56 (2H, d, J=7.85 Hz), 8.06 (1H, s), 8.15-8.17 (2H, d, J=7.87 Hz);
Mass: [M+H]$^+$: 464.2, 466:2.

Step (vii): Preparation of 1-[(2-Bromophenyl)sulfonyl]-5-methoxy-3-[(1-piperazinyl)methyl]-1H-indole dimesylate dihydrate

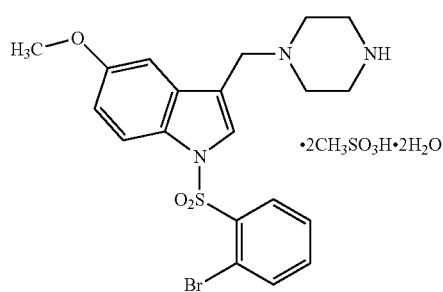

(II)

·2CH$_3$SO$_3$H·2H$_2$O

Acetone (24.15 L) was taken in a Glass Lined Reactor at 25-30° C., followed by 1-[(2-Bromo phenyl)sulfonyl]-5-methoxy-3-[(1-piperazinyl)methyl]-1H-indole dimesylate (obtained in the above step) (1.61 Kg) and the resulting mass was stirred to obtain slurry. DM water (4.0 L) was added to the reactor and then the mass temperature was raised to reflux temperature (56.0-57.5° C.). A clear solution was obtained at reflux. It was maintained for 15 minutes. The mass was cooled to 45-50° C. and added activated carbon (161 grams) to the mass and stirred the mass for 45 minutes at reflux temperature. It was filtered hot into another reactor, which was maintained at 50° C. The clear filtrate was allowed to cool on its own, under nitrogen blanket. Solids separated when the mass temperature was ~44° C. The mass was allowed to cool to room temperature (30-35° C.) and then it was further cooled at 10-12° C. for 2 hours. The product was centrifuged, washed with acetone (5 L) and sucked well. The wet product (weight: 1.5 Kg) was spread into trays and dried in a tray drier at 40-45° C. for 7.5 hours, till organic volatile impurities are below the allowable limits. Weight of the dry product obtained:

1.3 Kg. Yield: ~76.5%
Purity: 99.98%;
Melting range (° C.): 203.8-205.3;
Salt content (Dimesylate): 28.26%;
Moisture Content: 5.2%;
TGA: 4.9%;
$^1$H-NMR (D$_2$O, δ ppm): 2.65 (6H, s), 3.48 (8H, bm), 3.71 (3H, s), 4.48 (2H, s), 6.77-6.80 (1H, dd, J=9.18, 2.24 Hz), 7.12-7.13 (1H, d, J=2.12 Hz), 7.35-7.37 (1H, d, J=9.06 Hz), 7.37-7.41 (1H, t, =7.98 Hz), 7.46-7.50 (1H, t, J=7.66 Hz), 7.57-7.58 (1H, d, J=7.86 Hz), 8.06 (1H, s), 8.17-8.20 (1H, dd, J=7.95, 0.87 Hz),
Mass [M+H]$^+$: 464.2, 466.1;

Biological Assays

Example 3: Functional Assay for Human 5-HT$_6$ Receptor

Pharmacological data of compounds of formula (I) and formula (II) can be tested according to the following the experimental procedure.

Materials and Methods:
Receptor Source: Human recombinant expressed in CHOK1 cells
Reference agonist: Serotonin (5-HT)
Final ligand concentration—[10 μM]
Incubation Conditions:

Cell based reporter gene functional assay is performed using a validated cell line. Plate the cells and incubate overnight in complete medium. Next day incubate the cells in serum free medium (Ham's F12 without serum) for 18-24 hours. Perform the assay in OptiMEM medium by incubating the cells with 10 μM serotonin and compounds (1 nM to 10 μM) for 4 hours. Harvest the cells, lyse with lysis buffer and measure the luciferase activity using Perkin Elmer Victor Light Luminometer. Determine the binding affinity ($K_b$) value using the reporter activity measured as light units (Luminescence), analyze using nonlinear regression analysis with the analysis program Prism 4 (GraphPad software).

| Example Number | $K_b$ (nM) |
|---|---|
| 1. | 10.9 nM |
| 2. | 9.8 nM |

LITERATURE REFERENCES

Molecular Brain Research, 2001, 90, 110-117; British Journal of Pharmacology, 2006, 148, 1133-1143.

Example 4: Radial Arm Maze

The cognition enhancing properties of formula (I) and formula (II) of this invention were estimated by using this model.

Radial arm maze consists of a central hub of 45 centimeter diameter. Each arm was of dimension 42.5×15×24 centimeter. The maze was elevated to a height of 1 meter above the ground. The animals were placed on a restricted diet until they reached approximately 85% of their free feeding weight. During this diet restriction period animals were habituated to the novel feed (pellets). Once the rats reached approximately 85% of their free feeding weight rats were habituated to the maze on the 1$^{st}$ and 2$^{nd}$ day. The animals that did not eat the pellets were rejected from the study. Animals were randomized on day 2. On the subsequent days the treatment was given as per the allotment. Each animal was introduced into the maze individually for a period of 10 minutes. The arms were baited only once and the animal had to learn the rule that repeated arm entries would not be rewarded. The trial ended once the rat had visited 16 arms or 10 minutes were over or all the pellets were eaten. The arm entries were recorded using the software.

| Example Number | Reversal of Scopolamine Induced amnesia - Effective dose range |
| --- | --- |
| 1. | 10-20 mg/kg, p.o. |
| 2. | 5-20 mg/kg, p.o. |

We claim:

1. A compound having formula (I), 1-[(2-Bromophenyl)sulfonyl]-5-methoxy-3-[(1-piperazinyl)methyl]-1H-indole; wherein said compound is an active metabolite of 1-[(2-bromophenyl)sulfonyl]-5-methoxy-3-[(4-methyl-1-piperazinyl)methyl]-1H-indole dimesylate monohydrate

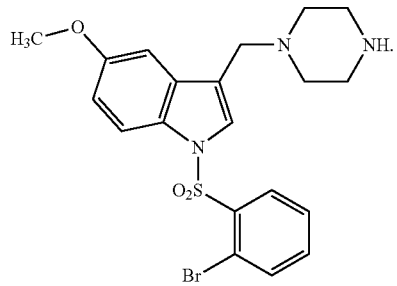
(I)

2. A process for the preparation of a compound of formula (I) as claimed in claim 1, which comprises:

Step (i): reacting N-Boc piperazine of formula 1

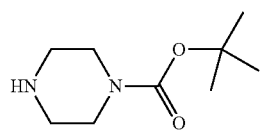
1 in presence of acetic acid and aqueous formaldehyde of formula 2 to obtain Mannich adduct;

HCHO  2

Step (ii): reacting the Mannich adduct with 5-methoxy-indole of formula 3

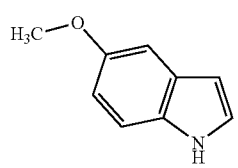
3 in presence of methanol to obtain 3-[(1-t-Butyloxycarbonyl piperazin-4-yl)methyl]-5-methoxy-1H-indole of formula 4;

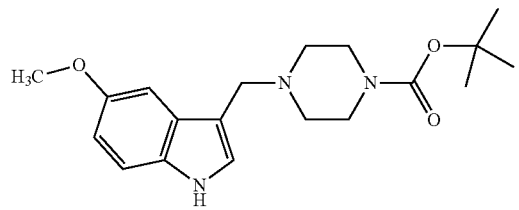
4

Step (iii): purification of 3-[(1-t-Butyloxycarbonyl piperazin-4-yl)methyl]-5-methoxy-1H-indole of formula 4 by using n-hexane;

Step (iv): reacting the above obtained 3-[(1-t-Butyloxycarbonyl piperazin-4-yl)methyl]-5-methoxy-1H-indole of formula 4 with 2-bromophenylsulfonyl chloride of formula 5;

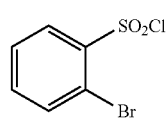
5 in tetrahydrofuran in presence of potassium hydroxide to obtain 1-[(2-Bromophenyl)sulfonyl]-5-methoxy-3-[(1-t-butyloxycarbonyl piperazin-4-yl)methyl]-1H-indole of formula 6;

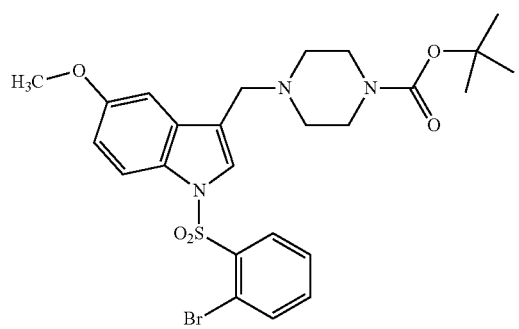
6

Step (v): purification of 1-[(2-Bromophenyl)sulfonyl]-5-methoxy-3-[(1-t-butyloxycarbonyl piperazin-4-yl)methyl]-1H-indole of formula 6 by using isopropanol and methanol;

Step (vi): converting the above obtained 1-[(2-Bromophenyl)sulfonyl]-5-methoxy-3-[(1-t-butyloxycarbonyl piperazin-4-yl)methyl]-1H-indole of formula 6 in presence of absolute ethanol and aqueous hydrochloric acid to obtain 1-[(2-Bromophenyl)sulfonyl]-5-methoxy-3-[(1-piperazinyl)methyl]-1H-indole dihydrochloride of formula 8;

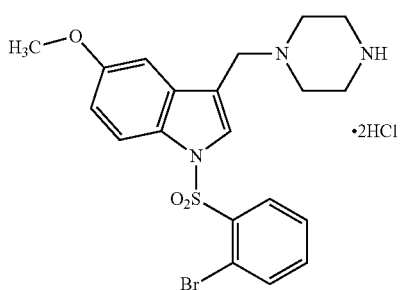

Step (vii): the above obtained 1-[(2-Bromophenyl)sulfonyl]-5-methoxy-3-[(piperazin-1-yl)methyl]-1H-indole dihydrochloride of formula 8 is dissolved in water and basified to pH 10.5 to 11 by adding 40% (w/w) lye solution to obtain 1-[(2-Bromophenyl)sulfonyl]-5-methoxy-3-[(1-piperazinyl)methyl]-1H-indole of formula (I).

3. A compound of the general formula (II),

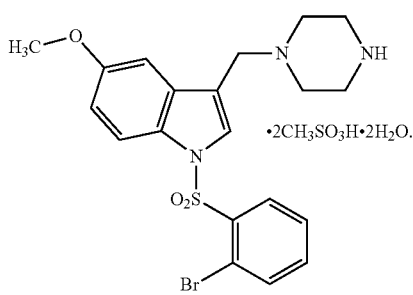

4. A process for the preparation of a compound of formula (II) as claimed in claim 3, which comprises:

Step (i): reacting N-Boc piperazine of formula 1

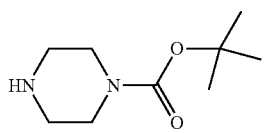

in presence of acetic acid and aqueous formaldehyde of formula 2 to obtain Mannich adduct;

HCHO     2

Step (ii): reacting the Mannich adduct with 5-methoxy-indole of formula 3

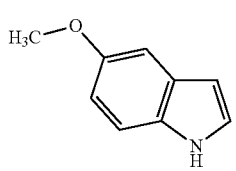

in presence of methanol to obtain 3-[(1-t-Butyloxycarbonyl piperazin-4-yl)methyl]-5-methoxy-1H-indole of formula 4;

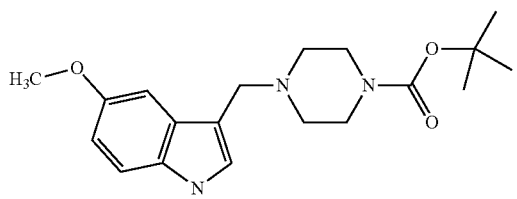

Step (iii): purification of 3-[(1-t-Butyloxycarbonyl piperazin-4-yl)methyl]-5-methoxy-1H-indole of formula 4 by using n-hexane;

Step (iv): reacting the above obtained 3-[(1-t-Butyloxycarbonyl piperazin-4-yl)methyl]-5-methoxy-1H-indole of formula 4 with 2-bromophenylsulfonyl chloride of formula 5;

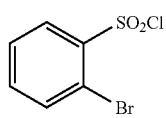

in tetrahydrofuran in presence of potassium hydroxide to obtain 1-[(2-Bromophenyl)sulfonyl]-5-methoxy-3-[(1-t-butyloxycarbonyl piperazin-4-yl)methyl]-1H-indole of formula 6;

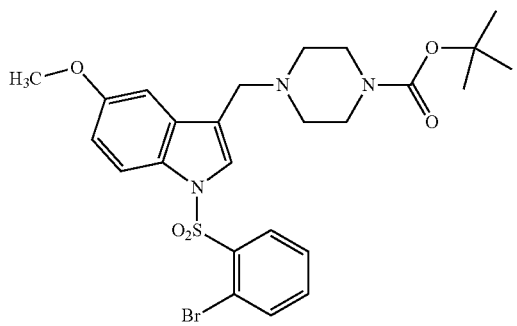

Step (v): purification of 1-[(2-Bromophenyl)sulfonyl]-5-methoxy-3-[(1-t-butyloxycarbonyl piperazin-4-yl) methyl]-1H-indole of formula 6 by using isopropanol and methanol;

Step (vi): converting the above obtained 1-[(2-Bromophenyl)sulfonyl]-5-methoxy-3-[(1-t-butyloxycarbonyl piperazin-4-yl)methyl]-1H-indole of formula 6 in presence of acetone and methanesulfonic acid of formula 7

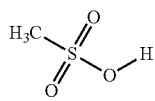

to obtain 1-[(2-Bromophenyl)sulfonyl]-5-methoxy-3-[(1-piperazinyl)methyl]-1H-indole dimesylate of formula 9;

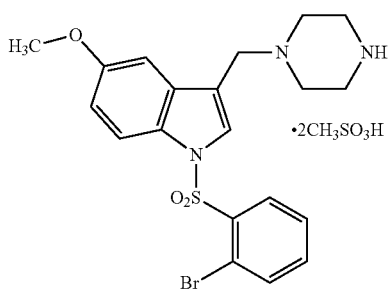

Step (vii): the above obtained 1-[(2-Bromophenyl)sulfonyl]-5-methoxy-3-[(1-piperazinyl)methyl]-1H-indole dimesylate of formula 9 is dissolved in water and acetone by heating to 55-60° C. to obtain 1-[(2-Bromophenyl)sulfonyl]-5-methoxy-3-[(1-piperazinyl)methyl]-1H-indole dimesylate dihydrate of formula (II).

5. A pharmaceutical composition comprising the compound according to claim 1 and pharmaceutically acceptable excipients.

6. The pharmaceutical composition according to claim 5, for the treatment of Alzheimer's disease, Attention deficient hyperactivity, Parkinson's disease and schizophrenia.

7. A method of treating Alzheimer's disease, Attention deficient hyperactivity, Parkinson's disease and schizophrenia, comprising the step of administering to a patient in need thereof an effective amount of a compound according to claim 1.

8. A pharmaceutical composition comprising a compound according to claim 3 and pharmaceutically acceptable excipients.

9. The pharmaceutical composition according to claim 8, for the treatment of Alzheimer's disease, Attention deficient hyperactivity, Parkinson's disease and schizophrenia.

10. A method of treating Alzheimer's disease, Attention deficient hyperactivity, Parkinson's disease and schizophrenia, comprising the step of administering to a patient in need thereof an effective amount of a compound according to claim 3.

11. A method for the treatment of a disease related to 5-$HT_6$ receptor where said disease is Alzheimer's disease, comprising the step of administering to a patient in need thereof an effective amount of a compound according to claim 3.

12. A method for the treatment of Alzheimer's disease, Attention deficient hyperactivity, Parkinson's disease and schizophrenia, comprising the step of administering to a patient in need thereof an effective amount of a compound according to claim 1.

13. A method for the treatment of a disease related to 5-$HT_6$ receptor where said disease is Attention deficient hyperactivity, comprising the step of administering to a patient in need thereof an effective amount of a compound according to claim 3.

14. A method for the treatment of a disease related to 5-$HT_6$ receptor where said disease is Parkinson's disease, comprising the step of administering to a patient in need thereof an effective amount of a compound according to claim 3.

15. A method for the treatment of a disease related to 5-$HT_6$ receptor where said disease is schizophrenia, comprising the step of administering to a patient in need thereof an effective amount of a compound according to claim 3.

* * * * *